PROCESS FOR PRODUCING α-ARYLALKANOIC ACID ESTER

This invention relates to a process for producing α-arylalkanoic acid esters, and more specifically, to a novel and improved process for producing α-arylalkanoic acid esters expressed by the following general formula $$Ar-\underset{\underset{R^1}{|}}{CH}-COOR^2 \qquad (I)$$

wherein Ar represents an aryl group which may be substituted, and $R^1$ and $R^2$, independently from each other, represent a lower alkyl group.

The α-arylalkanoates of general formula (I) are industrially very useful compounds which can be converted to useful medicines such as Ibuprofen, Naproxen, Ketoprofen and Fenoprofen known as analgesic and anti-inflammatory agents by, for example, saponification, or can be used as intermediates for synthesis of agricultural chemicals such as Fenvalerate known to have high activity as a pyrethroid insecticide.

A number of processes including one which goes through an aryl methylketone have been proposed heretofore for the production of these α-arylaklanoic acid derivatives, but have not proved to be entirely satisfactory because they involve a multi-step procedure with a troublesome operation.

As an improvement over these processes, a process is known which comprises converting an aryl halide to an aryl lithium or magnesium compound, reacting it with an equimolar amount of a zinc halide, a copper halide or a cadmium halide to form the corresponding aryl metal salt, and reacting the aryl metal salt with an α-haloester to give an α-arylalkanoic acid ester [see, for example, U.S. Pat. Nos. 3,663,584, 3,658,863 and 3,658,858, and J. Org. Chem., 33, 1675 (1968)]. This process is characterized by giving the desired α-arylalkanoic acid derivatives with relatively short steps, but are not industrially feasible in view of the cost of the zinc, copper or cadmium halides and the need to treat industrial wastes containing these compounds. Furthermore, as shown in Comparative Examples 3, 4, 7 and 8 given hereinafter, the yields of the desired products are not high. Hence, this type of process is not industrially satisfactory.

Some processes have also been reported for obtaining α-arylalkanoic acids by reacting aryl halides with metallic magnesium, and reacting the resulting Grignard reagents with metal salts of α-halopropionic acids (lithium, sodium, magnesium or calcium salts) (see, for example, U.S. Pat No. 3,959,364). These processes, however, require a step of converting an α-halopropionic acid into a metal salt, and the yield of the final product is not entirely satisfactory (see Comparative Examples 1 and 2). Another defect is that when a compound having a double bond such as an alkenylphenylalkanoic acid (e.g., prenylphenylpropionic acid) is to be produced, the double bond of the resulting α-arylpropionic acid, unlike the corresponding ester, tends to be isomerized by heat or its own acidity during distillation for its purification.

A process has also been proposed for producing an α-arylpropionic acid which comprises reacting an aryl magnesium bromide with $$\underset{\underset{Br}{|}}{CH_3CHCOOMgCl} \text{ (or Br)}$$

obtained by treating an α-bromopropionic acid with a Grignard reagent, and rapidly cooling the resulting reaction mixture with an acid (see, for example, U.S. Pat. No. 4,144,387). This process, however, has the defect that it requires a step of preparing a mixed magnesium halide complex of an α-bromopropionic acid, and one equivalent of the relatively expensive Grignard reagent must be used in this step, resulting in an increase in the cost of starting chemicals. In addition, the yield of the desired product is by no means satisfactory (see Comparative Examples 5 and 6).

We have made assiduous investigations about an industrially advantageous process for producing α-arylalkanoic acid esters of general formula (I) which are synthetic intermediates for useful chemical compounds such as medicines or agricultural chemicals and are easy to separate and purify. These investigations have led to the discovery that while the reaction of a Grignard reagent obtained from an aryl halide and metallic magnesium with an α-haloalkanoic acid ester in the absence of catalyst gives a product in a very low yield (see Comparative Examples 9 and 10), the addition of a catalytic amount of a nickel compound to the reaction system surprisingly makes the reaction proceed very smoothly under mild conditions and gives the desired α-arylalkanoic acid ester of general formula (I) in good yields.

Thus, according to this invention, there is provided a process for producing an α-arylalkanoic acid ester represented by the following formula $$Ar-\underset{\underset{R^1}{|}}{CH}-COOR^2 \qquad (I)$$

wherein Ar represents an aryl group which may be optionally substituted, and $R^1$ and $R^2$, independently from each other, represent a lower alkyl group, which comprises reacting a Grignard reagent prepared from an aryl halide represented by the following formula $$Ar-X^1 \qquad (II)$$

wherein Ar is as defined above, and $X^1$ represents a halogen atom, and magnesium with an α-haloalkanoic acid ester represented by the following formula $$R^1-\underset{\underset{X^2}{|}}{CH}-COOR^2 \qquad (III)$$

wherein $R^1$ and $R^2$ are as defined above, and $X^2$ represents a halogen atom, said reaction between the Grignard reagent and the α-haloalkanoic acid ester being carried out in the presence of a nickel compound.

The process of this invention can be shown by the following reaction equation.

United States Patent [19]

Amano et al.

[11] 4,433,160
[45] Feb. 21, 1984

[54] PROCESS FOR PRODUCING α-ARYLALKANOIC ACID ESTER

[75] Inventors: Takehiro Amano, Urawa; Kensei Yoshikawa, Kitamoto; Tatsuhiko Sano; Yutaka Ohuchi, both of Ohmiya; Michihiro Ishiguro, Kurashiki; Manzo Shiono, Kurashiki; Yoshiji Fujita, Kurashiki; Takashi Nishida, Kurashiki, all of Japan

[73] Assignee: Taisho Pharmaceutical Company, Ltd., Tokyo, Japan

[21] Appl. No.: 411,480

[22] Filed: Aug. 25, 1982

[30] Foreign Application Priority Data

Aug. 26, 1981 [JP] Japan .................. 56-134781

[51] Int. Cl.³ ............................................. C07L 69/76
[52] U.S. Cl. ..................................... 560/56; 560/100; 560/101; 560/102; 560/104; 560/105; 562/493; 562/495; 562/496; 546/89; 546/121; 548/224; 548/565; 549/79
[58] Field of Search ................. 560/105, 56, 100, 101, 560/102, 104, 105; 562/493, 495, 496; 546/89, 121; 548/224, 565; 549/79

[56] References Cited

U.S. PATENT DOCUMENTS 2,873,275  2/1959  Ramsden ............................ 560/105
2,921,939  1/1960  Ramsden ............................ 560/105

Primary Examiner—Paul J. Killos
Attorney, Agent, or Firm—Wenderoth, Lind & Ponack

[57] ABSTRACT

A process for producing an α-arylalkanoic acid ester represented by the general formula

$$Ar-\overset{R^1}{\underset{|}{C}H}-COOR^2 \qquad (I)$$

wherein Ar represents an aryl group which may optionally be substituted, and $R^1$ and $R^2$, independently from each other, represent a lower alkyl group, which comprises reacting a Grignard reagent prepared from an aryl halide of the general formula

$$Ar-X^1 \qquad (II)$$

wherein Ar is as defined above and $X^1$ represents a halogen atom, and magnesium, with an α-haloalkanoic acid ester of the general formula

$$R^1-\underset{\underset{X^2}{|}}{C}H-COOR^2 \qquad (III)$$

wherein $R^1$ and $R^2$ are as defined above, and $X^2$ represents a halogen atom, said reaction of the Grignard reagent with the α-haloalkanoic acid ester of general formula (III) being carried out in the presence of a nickel compound.

8 Claims, No Drawings

-continued

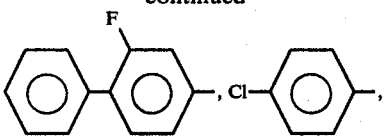

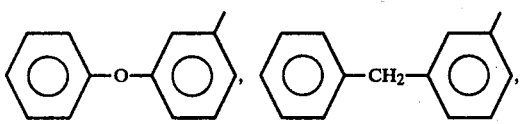

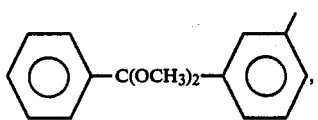

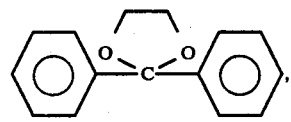

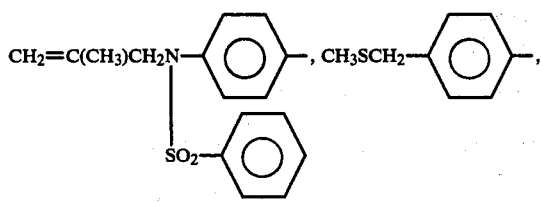

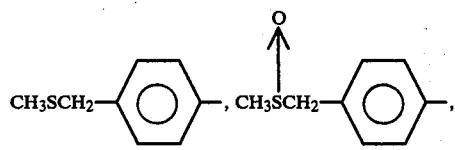

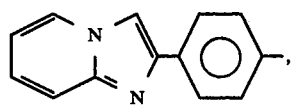

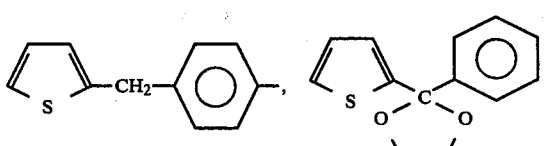

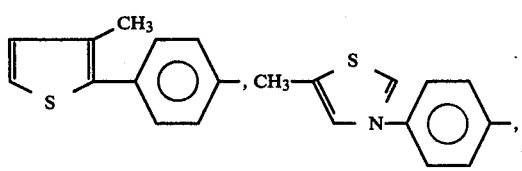

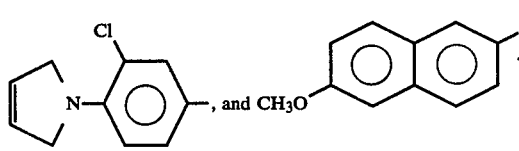

The "substituted aryl groups" also include aryl groups fused with hydrocarbon rings or heterocyclic rings having at least 1, preferably 1 or 2, hetero atom selected from nitrogen, oxygen and sulfur. Examples of the fused aryl groups are as follows:

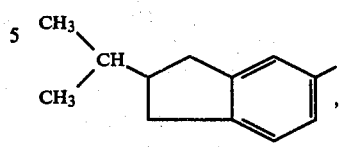

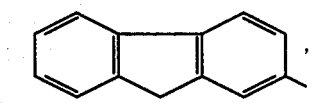

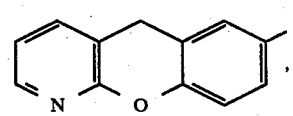

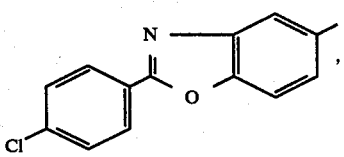

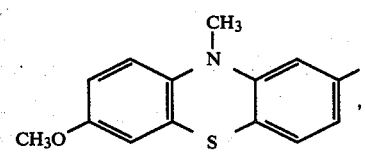

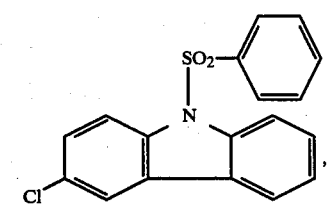

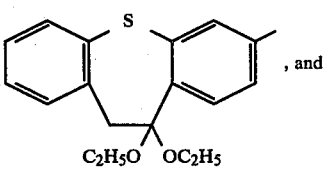

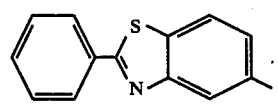, and

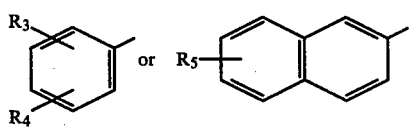

The term "lower", as used in the present specification and the appended claims, means that a group qualified thereby has not more than 8, preferably not more than 5, carbon atoms.

Examples of preferred aryl groups Ar in this invention include aryl groups of the following formula wherein $R_3$ represents a hydrogen atom, a halogen atom, a lower alkyl group, a lower alkenyl group, a phenyl group, a benzyl group, a lower alkoxy group, a phenoxy group or a ketalized benzoyl group, $R_4$ represents a hydrogen atom or a halogen atom (particularly a fluorine atom), and $R_5$ represents a hydrogen atom or a lower alkoxy group.

Examples of especially preferred aryl groups Ar include p-isobutylphenyl, p-prenylphenyl, p-(2-methyl-1-propenyl)phenyl, p-(2-methyl-2-propenyl)phenyl, p-chlorophenyl, m-benzylphenyl, m-phenoxyphenyl, 6-methoxy-2-naphthyl, and m-fluoro-p-biphenylyl groups.

$R^1$ and $R^2$ in general formulae (I) and (III) may be linear or branched lower alkyl groups such as methyl, ethyl, n-propyl, isopropyl, n-butyl, isobutyl, and t-butyl groups. The methyl group is especially preferred as $R^1$, and methyl, ethyl and tert-butyl groups are especially preferred as $R^2$.

The halogen atom $X^1$ is preferably a chlorine or bromine atom in view of the availability of the aryl halide of general formula (II). Examples of the halogen atom $X^2$ are chlorine, bromine and iodine atoms. Preferably, $X^2$ is a bromine atom in view of the reactivity and availability of the α-haloalkanoic acid ester of general formula (III).

In performing the process of this invention, the Grignard reagent may be prepared by a method known per se from metallic magnesium and the aryl halide of general formula (II). The preparation of the Grignard reagent may be carried out in a solvent as usual. The use of an ether solvent, such as tetrahydrofuran, tetrahydropyran, diethyl ether or diisopropyl ether, is particularly recommended. The reaction temperature for the preparation of the Grignard reagent may be selected generally from a range of about $-20°$ C. to about $160°$ C. It is preferred to use temperatures which permit controlling of a reaction exotherm, particularly about $0°$ C. to about $130°$ C. The amount of metallic magnesium used is not critical, but generally, it is from about 1 atomic equivalent to about 1.5 atomic equivalents based on the aryl halide of general formula (II). Magnesium commercially available for Grignard reaction is preferred as metallic magnesium. It is also possible to use powdery or granular magnesium or activated magnesium prepared from magnesium chloride and metallic potassium.

The resulting Grignard reagent can usually be used in the subsequent reaction without isolating it, namely while it contains the solvent.

According to this invention, the Grignard reagent prepared from the aryl halide of general formula (II) and metallic magnesium is reacted with the α-haloalkanoic acid ester of general formula (III). The characteristic feature of the process of this invention is that this reaction is carried out in the presence of a nickel compound.

Nickel compounds which are at least partly soluble in the reaction medium are preferably used. Examples of preferred nickel compounds are inorganic acid salts and organic acid salts of nickel, such as nickel halides (e.g., chloride, bromide and iodide), phosphine complexes with these halides, nickel fulfate, nickel nitrate, nickel carbonate, nickel formate, nickel acetate, and nickel acetylacetonate. Especially preferred are $NiCl_2$, $NiBr_2$, $[Ni(C_5H_7O_2)_2]$, $NiCl_2[P(C_6H_5)_3]_2$, and $NiCl_2[(C_6H_5)_2PCH_2CH_2CH_2P(C_6H_5)_2]$. The amount of the nickel compound as a catalyst is usually about 0.05 to about 10 mole %, preferably about 0.1 mole% to about 5 mole%, based on the Grignard reagent.

The reaction between the Grignard reagent and the α-haloalkanoic acid ester of general formula (III) may be carried out in the solvent used in the preparation of the Grignard reagent. As required, this solvent may be replaced by, or used in admixture with, an inert hydrocarbon solvent such as hexane and toluene or an aprotic polar solvent such as hexamethylphosphoric triamide.

The reaction temperature in the reaction of the Grignard reagent with the α-haloalkanoic acid ester of general formula (III) in the presence of the nickel catalyst can be freely chosen from a range of from about $-10°$ C. to about $80°$ C., preferably from about $0°$ C. to about $50°$ C. The amount of the α-haloalkanoic acid ester represented by general formula (III) is not critical, and can be varied widely according to the type of the Grignard reagent and/or the compound of general formula (III), the reaction conditions, etc. Generally, the amount of the compound of general formula (III) is conveniently from about 0.8 to about 1.3 moles, preferably from about 0.9 to about 1.0 mole, per mole of the aryl halide of general formula (II) used in the preparation of the Grignard reagent.

The resulting α-arylalkanoic acid ester of general formula (I) can be separated from the reaction mixture, and purified, by methods known per se, for example extraction, distillation, and chromatography.

Examples of typical α-arylalkanoic acid esters obtained by the process of this invention are listed below.

| Compound No. | | Elemental analysis Found (%) | Calculated (%) |
|---|---|---|---|
| (1) | $CH_3-CH(CH_3)-CH_2-\langle\text{phenyl}\rangle-CH(CH_3)-CO_2CH_2CH_3$ | C: 76.69<br>H: 9.42 | 76.88<br>9.46 |
| (2) | $\langle\text{phenyl}\rangle-CH_2-\langle\text{phenyl}\rangle-CH(CH_3)-CO_2CH_2CH_3$ | C: 80.39<br>H: 7.48 | 80.56<br>7.51 |
| (3) | $\langle\text{phenyl}\rangle-O-\langle\text{phenyl}\rangle-CH(CH_3)-CO_2CH_2CH_3$ | C: 75.51<br>H: 6.74 | 75.53<br>6.71 |

-continued

| Compound No. | Structure | Elemental analysis Found (%) | Calculated (%) |
|---|---|---|---|
| (4) | CH₃O-[naphthyl]-CH(CH₃)-CO₂CH₂CH₃ | C: 74.27<br>H: 6.99 | 74.40<br>7.02 |
| (5) | [biphenyl]-CH(CH₃)-CO₂CH₂CH₃ | C: 80.20<br>H: 7.15 | 80.28<br>7.13 |
| (6) | [2-F-biphenyl]-CH(CH₃)-CO₂CH₂CH₃ | C: 75.04<br>H: 6.31 | 74.98<br>6.29 |
| (7) | CH₃-CH(CH₃)-CH₂-[C₆H₄]-CH(CH₃)-CO₂CH₃ | C: 76.27<br>H: 9.08 | 76.33<br>9.15 |
| (8) | [C₆H₅-O-C₆H₄]-CH(CH₃)-CO₂CH₃ | C: 74.87<br>H: 6.22 | 74.98<br>6.29 |
| (9) | CH₃O-[naphthyl]-CH(CH₃)-CO₂CH₃ | C: 73.35<br>H: 6.52 | 73.38<br>6.60 |
| (10) | [2-F-biphenyl]-CH(CH₃)-CO₂CH₃ | C: 74.41<br>H: 5.89 | 74.40<br>5.85 |
| (11) | CH₃-CH(CH₃)-CH₂-[C₆H₄]-CH(CH₃)-CO₂(CH₂)₂CH₃ | C: 77.19<br>H: 9.64 | 77.38<br>9.74 |
| (12) | CH₃-CH(CH₃)-CH₂-[C₆H₄]-CH(CH₃)-CO₂CH(CH₃)₂ | C: 77.30<br>H: 9.65 | 77.38<br>9.74 |
| (13) | CH₃-CH(CH₃)-CH₂-[C₆H₄]-CH(CH₃)-CO₂(CH₂)₃CH₃ | C: 77.80<br>H: 9.83 | 77.82<br>9.99 |
| (14) | CH₃-CH(CH₃)-CH₂-[C₆H₄]-CH(CH₃)-CO₂C(CH₃)₃ | C: 77.74<br>H: 9.81 | 77.82<br>9.99 |
| (15) | Cl-[C₆H₄]-CH(CH(CH₃)₂)-CO₂CH₂CH₃ | C: 64.93<br>H: 7.26 | 64.86<br>7.12 |
| (16) | Cl-[C₆H₄]-CH(CH(CH₃)₂)-CO₂CH₃ | C: 63.44<br>H: 6.63 | 63.58<br>6.67 |
| (17) | (CH₃)₃C-[C₆H₄]-CH(CH(CH₃)₂)-CO₂CH₂CH₃ | C: 77.76<br>H: 9.92 | 77.82<br>9.99 |
| (18) | CH₃-CH(CH₃)-CH=CH-[C₆H₄]-CH(CH₃)-CO₂CH₃ | C: 76.92<br>H: 8.29 | 77.03<br>8.31 |
| (19) | CH₃-CH(CH₃)-CH=C-[C₆H₄]-CH(CH₃)-CO₂CH₂CH₃ | C: 77.51<br>H: 8.63 | 77.55<br>8.68 |

-continued

| Compound No. | Structure | Elemental analysis Found (%) | Calculated (%) |
|---|---|---|---|
| (20) | CH₃–C(CH₃)=CH₂–⟨C₆H₄⟩–CH(CH₃)–CO₂C(CH₃)₃ | C: 78.37 H: 9.28 | 78.42 9.29 |
| (21) | CH₃–C(=CH₂)=CH–⟨C₆H₄⟩–CH(CH₃)–CO₂CH₂CH₃ | C: 77.39 H: 8.53 | 77.55 8.68 |
| (22) | CH₃–C(CH₃)=CHCH₂–⟨C₆H₄⟩–CH(CH₃)–CO₂CH₃ | C: 77.46 H: 8.60 | 77.55 8.68 |
| (23) | CH₃–C(CH₃)=CHCH₂–⟨C₆H₄⟩–CH(CH₃)–CO₂CH₂CH₃ | C: 77.84 H: 8.92 | 78.01 9.00 |
| (24) | CH₃–C(CH₃)=CHCH₂–⟨C₆H₄⟩–CH(CH₃)–CO₂C(CH₃)₃ | C: 78.78 H: 9.52 | 78.79 9.55 |
| (25) | C₆H₅–CH(CH₃)–CO₂CH₂CH₃ | C: 74.06 H: 7.91 | 74.13 7.92 |
| (26) | (imidazo[1,2-a]pyridin-2-yl)–⟨C₆H₄⟩–CH(CH₃)–CO₂–CH₂–CH₃ | C: 73.54 H: 6.07 | 73.45 6.16 |
| (27) | (pyrano[2,3-b]pyridine)–CH₂–⟨C₆H₃⟩–CH(CH₃)–CO₂CH₂CH₃ | C: 72.21 H: 6.17 | 72.07 6.05 |
| (28) | (3-methylthien-2-yl)–CH(CH₃)–CO₂CH₂CH₃ | C: 60.39 H: 7.04 | 60.57 7.12 |
| (29) | (2,5-dihydropyrrol-1-yl)–⟨3-Cl-C₆H₃⟩–CH(CH₃)CO₂CH₂CH₃ | C: 64.51 H: 6.53 | 64.40 6.49 |
| (30) | (fluoren-2-yl)–CH(CH₃)CO₂CH₂CH₃ | C: 81.02 H: 6.73 | 81.17 6.81 |
| (31) | [2-(4-chlorophenyl)benzoxazol-6-yl]–CH(CH₃)CO₂CH₂CH₃ | C: 65.18 H: 4.69 | 65.36 4.88 |

The α-arylalkanoic acid ester of general formula (I) obtained by the process of this invention readily undergoes hydrolysis under general hydrolyzing conditions for esters to give the α-arylalkanoic acid or its salt (see Referential Example 1).

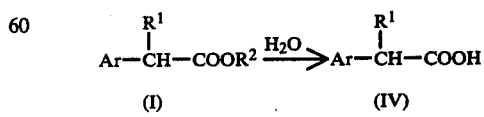

$$\underset{(I)}{Ar-\overset{R^1}{\underset{|}{CH}}-COOR^2} \xrightarrow{H_2O} \underset{(IV)}{Ar-\overset{R^1}{\underset{|}{CH}}-COOH}$$

The resulting α-arylalkanoic acids of general formula (IV) include many compounds useful as medicines such as Ibuprofen, Naproxen, Ketoprofen, Fenoprofen and Flurbiprofen. A compound of general formula (IV) in which Ar is a p-chlorophenyl group and $R^1$ is an isopropyl group is an important intermediate for the synthesis of Fenvalerate which is useful as an insecticide.

The following examples illustrate the present invention more specifically.

EXAMPLE 1

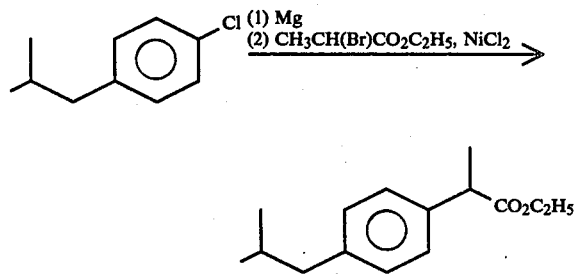

Under a nitrogen atmosphere, an about 1 M tetrahydrofuran (THF) solution of a Grignard reagent prepared from 0.29 g of magnesium turnings for Grignard reaction and 1.69 g of p-chloroisobutylbenzene was added dropwise to a solution composed of 1.81 g of ethyl α-bromopropionate, 0.013 g of $NiCl_2$ and 4 ml of THF with stirring. After the addition, the mixture was stirred for 1 hour, and an aqueous solution of ammonium chloride was added. The mixture was extracted with diethyl ether. The ethereal extract was washed with an aqueous solution of sodium chloride, dried, concentrated, and purified by silica gel column chromatography to give 1.17 g (yield 50%) of ethyl α-(p-isobutylphenyl)propionate [compound (1)] having the following NMR spectrum.

NMR spectrum $\delta_{CDCl_3}^{HMS}$: 0.83 (d, J=7 Hz, 6H); 1.07 (t, J=7 Hz, 3H); 1.39 (d, J=7 Hz, 3H); 1.6–2.0 (m, 1H); 2.36 (d, J=7 Hz, 2H); 3.59 (q, J=7 Hz, 1H); 4.01 (q, J=7 Hz, 2H); 6.9–7.25 (m, 4H).

EXAMPLES 2 TO 4

Ethyl α-(m-benzylphenyl)propionate [compound (2)], ethyl α-(m-phenoxyphenyl)propionate [compound (3)], and ethyl α-(6-methoxy-2-naphthyl)propionate [compound (4)] were prepared respectively in the same way as in Example 1 except that 2.03 g of m-benzylchlorobenzene (Example 2), 2.49 g of m-phenoxybromobenzene and 2.35 g of 2-bromo-6-methoxynaphthalene (Example 4) were used respectively instead of 1.69 g of p-chloroisobutylbenzene. The amounts and NMR spectra of these products are shown in Table 1.

TABLE 1

| Example | Compound | Amount (g)* | NMR spectrum ($\delta_{CDCl_3}^{HMS}$) |
|---|---|---|---|
| 2 | (2) | 1.29 (48.1%) | 1.01 (t, J=7Hz, 3H), 1.35 (d, J=7Hz, 3H), 3.54 (q, J=7Hz, 1H), 3.83 (s, 2H), 3.96 (q, J=7Hz, 2H), 6.85–7.3 (m, 9H). |
| 3 | (3) | 1.31 (48.5%) | 1.05 (t, J=7Hz, 3H), 1.36 (d, J=7Hz, 3H), 3.56 (q, J=7Hz, 1H), 3.98 (q, J=7Hz, 2H), 6.68–7.4 (m, 9H). |
| 4 | (4) | 1.22 (47.3%) | 1.11 (t, J=7Hz, 3H), 1.49 (d, J=7Hz, 3H), 3.75 (q, J=7Hz, 1H), 3.83 (s, 3H), 4.06 (q, J=7Hz, 2H), 7.07– |

TABLE 1-continued

| Example | Compound | Amount (g)* | NMR spectrum ($\delta_{CDCl_3}^{HMS}$) |
|---|---|---|---|
| | | | 7.75 (m, 6H). |

*The parenthesized figures show yields in percent.

EXAMPLES 5 TO 11

In the same way as in Example 1, ethyl α-(p-isobutylphenyl)propionate was prepared from p-chloroisobutylbenzene and ethyl α-(bromo)propionate except that each of the nickel compounds indicated in Table 2 was used instead of 0.013 g of $NiCl_2$. The amounts of the product (the parenthesized figures show yields) are shown in Table 2.

TABLE 2

| Example | Nickel compound (amount) | Amount of ethyl (α-(p-isobutylphenyl)-propionate (g) |
|---|---|---|
| 5 | $NiSO_4$ (0.016 g) | 1.04 (44.4%) |
| 6 | $Ni(OCOCH_3)_2$ (0.018 g) | 1.14 (48.7%) |
| 7 | $Ni(OCOH)_2$ (0.015 g) | 1.01 (43.2%) |
| 8 | $NiCl_2[(C_6H_5)_2P(CH_2)_3P(C_6H_5)_2]$ (0.054 g) | 1.15 (49.1%) |
| 9 | $NiCl_2[(C_6H_5)_2P(CH_2)_2P(C_6H_5)_2]$ (0.053 g) | 1.13 (48.3%) |
| 10 | $NiCl_2[(CH_3)_2P(CH_2)_3P(CH_3)_2]$ (0.029 g) | 1.15 (49.1%) |
| 11 | $Ni(NO_3)_2$ (0.018 g) | 1.17 (50%) |

EXAMPLE 12

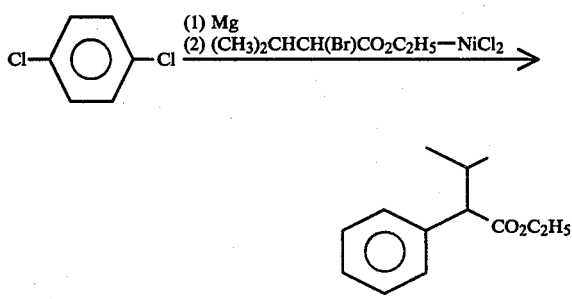

Ethyl α-(p-chlorophenyl)isovalerate was obtained in an amount of 0.71 g (yield 26.4%) in the same way as in Example 1 except that 1.47 g of p-dichlorobenzene was used instead of 1.69 g of p-chloroisobutylbenzene, and 2.09 g of ethyl α-bromoisovalerate was used instead of 1.81 g of ethyl α-bromopropionate.

EXAMPLE 13

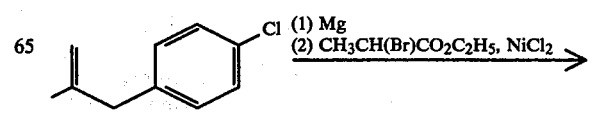

-continued

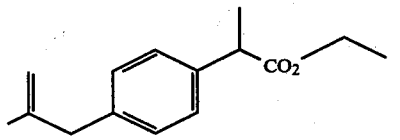

Under a nitrogen atmosphere, 5 ml of dry THF and 0.3 ml of ethyl bromide were added to 2.92 g of magnesium turnings for Grignard reaction, and the mixture was stirred. Heat was generated and the temperature of the mixture rose. Then, a solution composed of 16.65 g of p-chloro-(2-methyl-2-propenyl)benzene and 2 ml of THF was added dropwise, and the temperature of the mixture was raised to 130° C. Some amount of THF was added, and the mixture was heated under reflux at 100° C. for 4 hours. After cooling, 60 ml of THF was added, and the resulting reaction mixture was added dropwise to a solution composed of 18.1 g of ethyl α-bromopropionate, 0.065 g of nickel chloride and 40 ml of THF. After the addition, the mixture was stirred for 1 hour, and an aqueous solution of ammonium chloride was added. The mixture was extracted with diethyl ether. The ethereal extract was washed with an aqueous solution of sodium chloride, dried, concentrated and distilled to give 11.3 g (yield 48.7%) of ethyl α-[p-(2-methyl-2-propenyl)phenyl]propionate having the following properties.

Boiling point: 80° to 88° C./0.3 mmHg.

NMR spectrum $\delta_{CDCl_3}{}^{HMS}$: 1.11 (t, J=7 Hz, 3H); 1.41 (d, J=7 Hz, 3H); 1.60 (s, 3H); 3.23 (s, 2H); 3.61 (q, J=7 Hz, 1H); 4.03 (q, J=7 Hz, 2H); 4.6–4.8 (m, 2H); 6.98–7.26 (m, 4H).

EXAMPLE 14

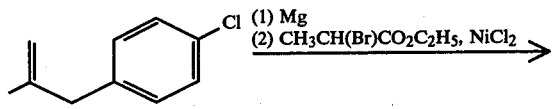

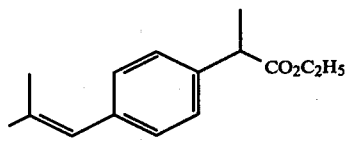

Under an atmosphere of nitrogen, 0.1 g of ethyl bromide was added to a solution composed of 0.27 g of magnesium turnings for Grignard reaction, 1.67 g of p-chloro-(2-methyl-1-propenyl)benzene and 1 ml of THF. After the starting of the reaction, the mixture was heated to 115° C. THF was added little by little so as to maintain the temperature in the range of 110° to 120° C., and the mixture was maintained at this temperature for 4 hours. After cooling, 5 ml of THF was added. The resulting Grignard reagent solution was added dropwise to a solution composed of 1.81 g of ethyl α-bromopropionate, 0.013 g of nickel chloride and 4 ml of THF. After the addition, the mixture was stirred for 1 hour, and an aqueous solution of ammonium chloride was added. The mixture was extracted with diethyl ether. The ethereal extract was washed with an aqueous solution of sodium chloride, dried, and concentrated. The concentrate was purified by silica gel column chromatography to give 0.85 g (yield 36.6%) of ethyl α-[p-(2-methyl-1-propenyl)phenyl]propionate having the following NMR spectrum.

NMR spectrum $\delta_{CDCl_3}{}^{HMS}$: 1.12 (t, J=7 Hz, 3H); 1.42 (d, J=7 Hz, 3H); 1.73–1.9 (m, 6H); 3.61 (q, J=7 Hz, 1H); 4.03 (q, J=7 Hz, 2H); 6.12–6.27 (m, 1H); 7.0–7.3 (m, 4H).

EXAMPLE 15

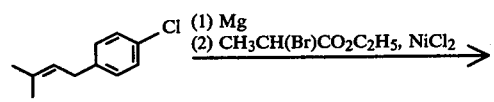

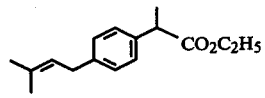

Under a nitrogen atmosphere, 0.3 ml of ethyl bromide was added to a mixture of 0.97 g of magnesium turning for Grignard reaction and 2 ml of THF. After the starting of the reaction, a solution composed of 6.01 g of p-chloroprenylbenzene and 1 ml of THF was added dropwise while maintaining the temperature at 115° to 130° C. After the addition, THF was added further as required, and the mixture was stirred at 110° to 120° C. for 4 hours. After cooling, 20 ml of THF was further added, and the resulting reaction mixture was added dropwise to a solution composed of 5.43 g of ethyl α-bromopropionate, 0.016 g of nickel chloride and 5 ml of THF. After the addition, the mixture was further stirred for 1 hour, and an aqueous solution of ammonium chloride was added. The mixture was extracted with diethyl ether. The ethereal extract was washed with an aqueous solution of sodium chloride, dried, concentrated and distilled to give 3.62 g (yield 49.1%) of ethyl α-(p-prenylphenyl)propionate.

Boiling point: 128° to 132° C./1.5 mmHg

NMR spectrum $\delta_{CDCl_3}{}^{HMS}$: 1.10 (t, J=7 Hz, 3H); 1.39 (d, J=7 Hz, 3H); 1.55–1.75 (m, 6H); 3.23 (d, J=7Hz, 2H); 3.58 (q, J=7 Hz, 1H); 4.02 (q, J=7 Hz, 2H); 5.1–5.4 (m, 1H); 6.97–7.3 (m, 4H).

EXAMPLE 16

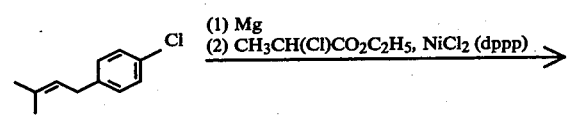

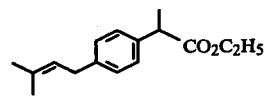

Ethyl α-(prenylphenyl)propionate was obtained in an amount of 2.52 g (yield 34.1%) in the same way as in Example 15 except that 4.10 g of ethyl α-chloropropionate and 0.06 g of [bis(diphenylphosphino)propane]nickel chloride were used instead of 5.43 g of ethyl α-bromopropionate and 0.016 g of nickel chloride, respectively.

EXAMPLE 17

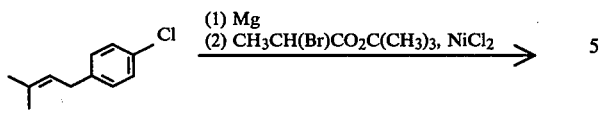

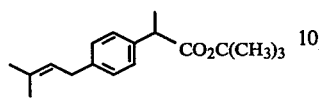

In the same way as in Example 15, 4.84 g (yield 58.9%) of t-butyl α-(p-prenylphenyl)propionate having the following NMR spectrum was obtained except that 6.27 g of t-butyl α-bromopropionate was used instead of 5.43 g of ethyl α-bromopropionate.

NMR spectrum $\delta_{CDCl_3}^{HMS}$: 1.23-1.4 (m, 12H); 1.55-1.73 (m, 6H); 3.22 (d, J=7 Hz, 2H); 3.48 (q, J=7 Hz, 1H); 5.25 (t, J=7 Hz, 1H); 6.95-7.2 (m, 4H).

EXAMPLE 18

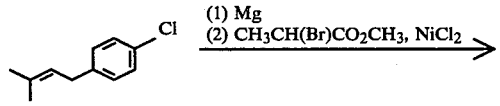

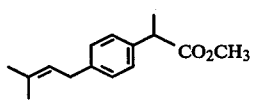

In the same way as in Example 15, 2.44 g (yield 35.1%) of methyl α-(p-prenylphenyl)propionate having the following NMR spectrum was obtained except that 5.01 g of methyl α-bromopropionate was used instead of 5.43 g of ethyl α-bromopropionate.

NMR spectrum $\delta_{CDCl_3}^{HMS}$: 1.38 (d, J=7 Hz, 3H); 1.55-1.7 (m, 6H); 3.22 (d, J=7 Hz, 2H); 3.54 (s, 3H); 3.58 (q, J=7 Hz, 1H); 5.1-5.35 (m, 1H); 6.93-7.2 (m, 4H).

EXAMPLES 19 TO 22

Ethyl α-(p-prenylphenyl)propionate was produced from p-chloroprenylbenzene and ethyl α-bromopropionate in the same way as in Example 15 except that each of the nickel compounds indicated in Table 3 was used instead of 0.016 g of NiCl$_2$. The amounts of the products with yields in the parentheses are shown in Table 3.

In Example 22, NiCl$_2$[P(C$_6$H$_5$)$_3$]$_2$ was used after it had been reacted with ethyl magnesium bromide to reduce it to a lower valency state.

TABLE 3

| Example | Nickel compound (amount) | Amount (g) of ethyl α-(p-prenylphenyl)-propionate formed (with yields, %) |
|---|---|---|
| 19 | NiBr$_2$ (0.022 g) | 3.25 (44.0%) |
| 20 | Nickel acetylacetonate (0.026 g) | 3.14 (42.5%) |
| 21 | NiCl$_2$[P(C$_6$H$_5$)$_3$]$_2$ (0.065 g) | 3.08 (41.7%) |
| 22 | A mixture of NiCl$_2$[P(C$_6$H$_5$)$_3$]$_2$ (0.65 g) and C$_2$H$_5$MgBr (0.2 mmole) was used in the form of a THF solution. | 3.58 (48.5%) |

REFERENTIAL EXAMPLE 1

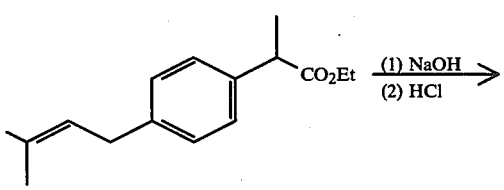

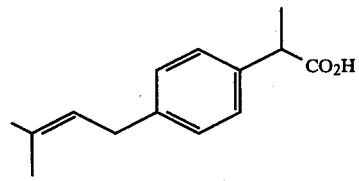

24.6 g of ethyl α-(p-prenylphenyl)propionate was dissolved in 250 ml of ethanol, and a solution composed of 6.0 g of sodium hydroxide and 10 ml of water was added. The mixture was stirred overnight at room temperature, and concentrated. Water was added, and the mixtue was washed with diethyl ether. The resulting aqueous layer was acidified with 1 N hydrochloric acid, and extracted with diethyl ether. The extract was washed with an aqueous solution of sodium chloride, dried, concentrated and distilled to give 19.5 g of α-(p-prenylphenyl)propionic acid having the following boiling point and NMR spectrum.

Boiling point: 130° to 135° C./0.1 mmHg

NMR spectrum $\delta_{CDCl_3}^{HMS}$: 1.45 (d, J=7 Hz, 3H); 1.66-1.8 (m, 6H); 3.32 (d, J=7 Hz, 2H); 3.68 (q, J=7 Hz, 1H); 5.2-5.45 (m, 1H); 7.05-7.35 (m, 4H); 11.83 (s, 1H).

The resulting α-(p-prenylphenyl)propionic acid is useful as an analgesic and anti-inflammatory agent with reduced gastrointestinal action (see U.S. Pat. No. 4,251,543).

COMPARATIVE EXAMPLE 1

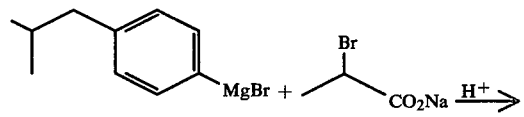

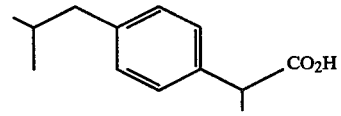

A suspension of 1.75 g of sodium α-bromopropionate in 20 ml of THF was added to 15 ml of a 0.67 M solution of p-isobutylphenyl magnesium bromide in THF. The mixture was heated under reflux for 1 hour, and then cooled. Then, 15 ml of water and then 5 ml of 20% sulfuric acid were added. The mixture was stirred for 10 to 15 minutes, and extracted with diethyl ether. The extract was washed with water, and then, extracted with a 1 N aqueous solution of potassium carbonate. The extract was washed with diethyl ether. The resulting aqueous layer was added to a mixture of 10 ml of concentrated hydrochloric acid and 20 ml of water, and the mixture was extracted with diethyl ether. The extract was washed with water, dried, concentrated and purified by silica gel column chromatography to give 0.21 g (yield 10.2%) of α-(p-isobutylphenyl)propionic acid.

COMPARATIVE EXAMPLE 2

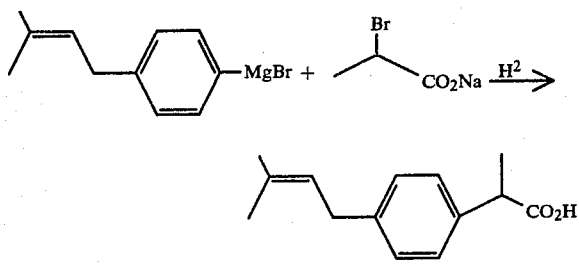

In the same way as in Comparative Example 1, 0.15 g (yield 6.9%) of α-[p-(3-methyl-2-butenyl)phenyl]propionic acid was obtained except that a 0.67 M solution of p-(3-methyl-2-butenyl)phenyl magnesium chloride in THF was used instead of the 0.67 M solution of p-isobutylphenyl magnesium bromide in THF.

COMPARATIVE EXAMPLE 3

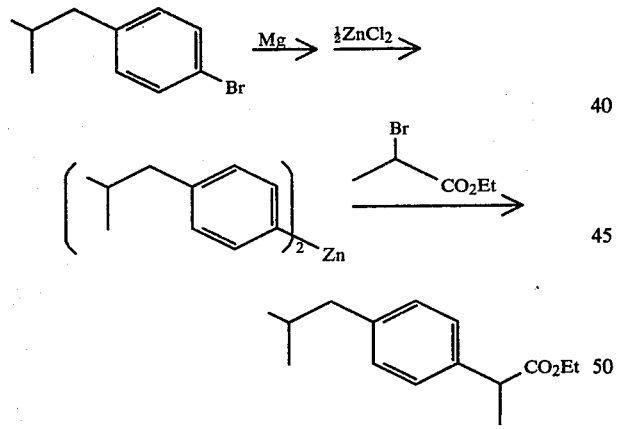

Under a nitrogen atmosphere, a solution of 10.2 g of p-bromoisobutylbenzene in 30 ml of benzene was added dropwise slowly to 1.2 g of magnesium turnings in 20 ml of THF at the refluxing temperature. To the resulting p-isobutylphenyl magnesium bromide solution was added 3.14 g of anhydrous zinc chloride in an atmosphere of nitrogen. When the temperature of the resulting mixture was maintained at 25° to 30° C. for 1 hour, a solution of di-(p-isobutylphenyl) zinc formed.

A solution of 9.96 g of ethyl α-bromopropionate in 5 ml of anhydrous benzene was added to the di-(p-isobutylphenyl) zinc solution. The reaction mixture was maintained at 50° to 55° C. for 15 hours in an atmosphere of nitrogen. The reaction mixture was then mixed with 175 ml of 1.5 N hydrochloric acid and subsequently with 65 ml of methylene chloride. The mixture was filtered, and the organic layer was separated. The acidic aqueous layer was extracted with two 30 ml portions of methylene chloride. The extracts were combined, washed with 50 ml of water, dried and concentrated. The resulting crude product was purified by silica gel column chromatography to give 2.05 g (yield 18.3%) of ethyl α-(p-isobutylpheny)propionate.

COMPARATIVE EXAMPLE 4

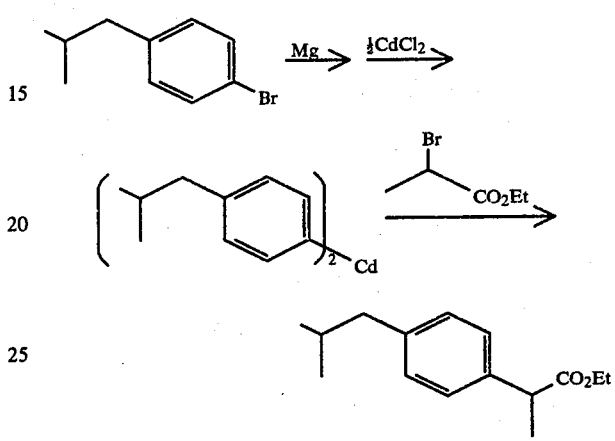

Ten grams of cadmium chloride was added to a Grignard reagent prepared from 21.7 g of p-bromoisobutylbenzene, 2.5 g of magnesium and 400 ml of THF. The mixture was refluxed for 10 minutes to give a solution of di-(p-isobutylphenyl)cadmium. A solution of 18 g of ethyl α-bromopropionate in 20 ml of THF was added to the reaction mixture which had been cooled. After standing at 20° C. for 24 hours, dilute hydrochloric acid was added to the mixture. The mixture was extracted with diethyl ether. The extract was washed with water, dried, concentrated, and purified by silica gel column chromatography to give 4.05 g (17.4%) of ethyl α-(p-isobutylphenyl)propionate.

COMPARATIVE EXAMPLE 5

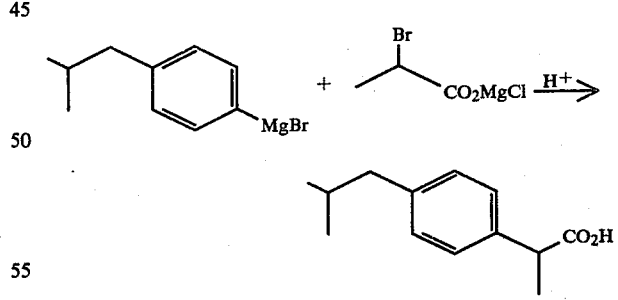

67 ml of a 1.5 M solution of a mixed magnesium chloride complex of α-bromopropionic acid in THF was slowly added to 67 ml of a 1.5 M solution cooled to 10° C. of p-isobutylphenyl magnesium bromide in THF at such a rate that the temperature of the mixture was maintained at not more than 55° C. The resulting slurry was stirred at 50° C. for 1 hour, and then heated under reflux to allow about 50% of THF to distill. The reaction mixture was cooled, and diethyl ether and dilute hydrochloric acid were added. The organic layer was washed with water, dried, concentrated, and purified by silica gel column chromatography to give 4.4 g (yield 21.3%) of α-(p-isobutylphenyl)propionic acid.

COMPARATIVE EXAMPLE 6

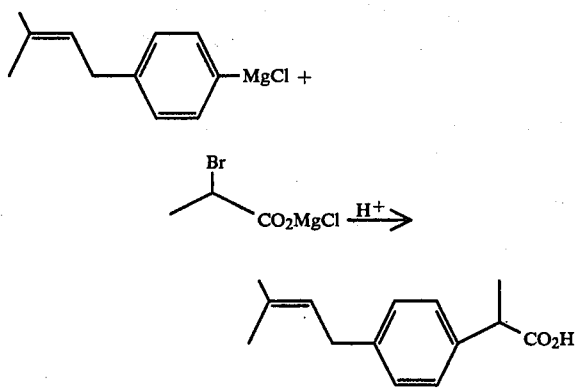

In the same way as in Comparative Example 5, 4.1 g (yield 18.8%) of α-[p-(3-methyl-2-butenyl)phenyl]propionic acid was obtained except that p-(3-methyl-2-butenyl)phenyl magnesium chloride was used instead of p-isobutylphenyl magnesium bromide.

COMPARATIVE EXAMPLE 7

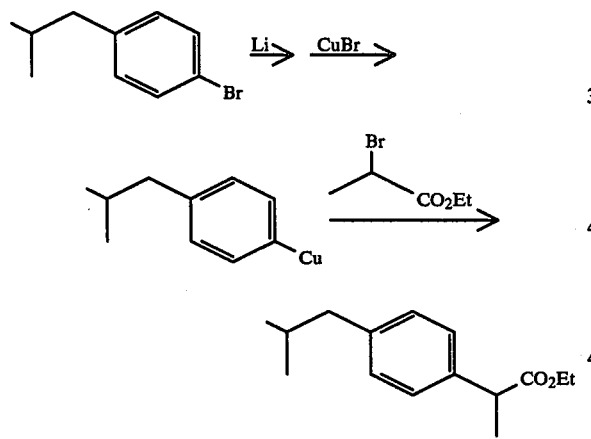

A solution of 21 g of p-bromoisobutylbenzene in 100 ml of THF was slowly added to 1.4 g of lithium metal in 100 ml of THF. When most of the lithium had reacted, 16 g of cuprous bromide was added. The suspension was stirred for 1 hour at about 20° C. to form p-isobutylphenyl copper (I). THF was then removed in vacuo while maintaining the temperature of the solution at less than 30° C. to yield p-isobutylphenyl copper (I). A solution of 18 g of ethyl α-bromopropionate in 50 ml of dimethylformamide was added to the residue, and the mixture was heated to 40° C. for 24 hours. The solvent was then removed in vacuo, and the residue was treated with an aqueous solution of ammonium chloride and diethyl ether. The organic layer was separated, dried, and concentrated in vacuo. The residue was purified by silica gel column chromatography to give 1.89 g (yield 8.2%) of ethy α-(p-isobutylphenyl)propionate.

COMPARATIVE EXAMPLE 8

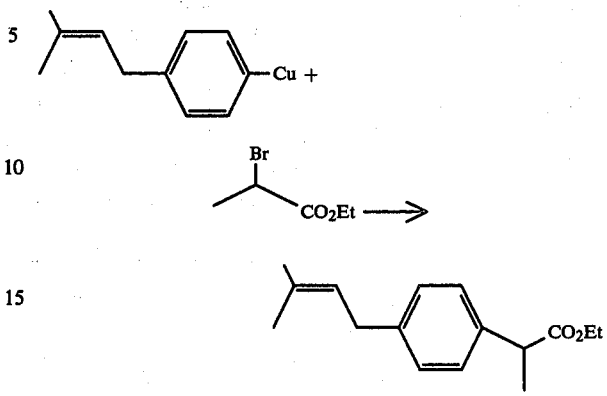

In the same way as in Comparative Example 7, p-(3-methyl-2-butenyl)phenyl copper (I) was reacted with ethyl α-bromopropionate. Ethyl α-[p-(3-methyl-2-butenyl)phenyl]propionate was obtained in an amount of 1.64 g (yield 6.7%).

COMPARATIVE EXAMPLE 9

Example 1 was followed except that NiCl$_2$ was not used. Ethyl α-(p-isobutylphenyl)propionate was obtained only in an amount of 0.077 g (yield 3.3%).

COMPARATIVE EXAMPLE 10

Example 12 was followed except that NiCl$_2$ was not used. Ethyl α-(p-chlorophenyl)isovalerate was obtained only in a trace amount.

What we claim is:

1. A process for producing an α-arylalkanoic acid ester represented by the general formula

wherein Ar represents an aryl group which may optionally be substituted, and R$^1$ and R$^2$, independently from each other, represent a lower alkyl group, which comprises reacting a Grignard reagent prepared from an aryl halide of the general formula

wherein Ar is as defined above and X$^1$ represents a halogen atom, and magnesium, with an α-haloalkanoic acid ester of the general formula

wherein R$^1$ and R$^2$ are as defined above, and X$^2$ represents a halogen atom, said reaction of the Grignard reagent with the α-haloalkanoic acid ester of general formula (III) being carried out in the presence of a catalytic amount of a nickel compound.

2. The process of claim 1 wherein the nickel compound is selected from the group consisting of nickel halides, phosphine complexes of nickel halides, nickel sulfate, nickel nitrate, nickel carbonate, nickel formate, nickel acetate and nickel acetylacetonate.

3. The process of claim 1 wherein the nickel compound is selected from the group consisting of $NiCl_2$, $NiBr_2$, $[Ni(C_5H_7O_2)_2]$, $NiCl_2[P(C_6H_5)_3]_2$ and $NiCl_2[(C_6H_5)_2PCH_2CH_2CH_2P(C_6H_5)_2]$.

4. The process of claim 1 wherein the amount of the nickel compound is about 0.05 to about 10 mole% based on the Grignard reagent.

5. The process of claim 1 wherein the reaction of the Grignard reagent with the α-haloalkanoic acid ester of general formula (III) is carried out at a temperature of about −10° C. to about 80° C.

6. The process of claim 1 wherein the reaction of the Grignard reagent with the α-haloalkanoic acid ester of general formula (III) is carried out at a temperature of from about 0° C. to about 50° C.

7. The process of claim 1 wherein the reaction of the Grignard reagent with the α-haloalkanoic acid ester of general formula (III) is carried out in an ether solvent.

8. The process of claim 1 wherein the amount of the α-haloalkanoic acid ester of general formula (III) is about 0.8 to about 1.3 moles per mole of the aryl halide of general formula (II) used in the prepanation of the Grignard reagent.

* * * * *

UNITED STATES PATENT AND TRADEMARK OFFICE
CERTIFICATE OF CORRECTION

PATENT NO.  : U.S.P. 4,433,160
DATED       : February 21, 1984
INVENTOR(S) : TAKEHIRO AMANO ET AL.

It is certified that error appears in the above-identified patent and that said Letters Patent is hereby corrected as shown below:

Kindly amend the above-identified patent as follows:

Front Page, left column, next to "[73]" change "Assignee: Taisho Pharmaceutical Company, Ltd., Tokyo, Japan"

to -- Assignees: Taisho Pharmaceutical Company, Ltd., Tokyo; Kuraray Co., Ltd., Okayama, both of Japan --.

Column 2, line 9, change "4,144,387" to -- 4,144,397 --.

Column 3, line 65, change the formula "  "

to -- 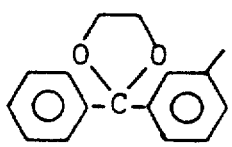 , 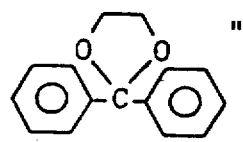 , --.

Column 5, line 20, change the formula

"  "

to --  --;

UNITED STATES PATENT AND TRADEMARK OFFICE
CERTIFICATE OF CORRECTION

PATENT NO. : U.S.P. 4,433,160
DATED : February 21, 1984
INVENTOR(S) : TAKEHIRO AMANO ET AL.

It is certified that error appears in the above-identified patent and that said Letters Patent is hereby corrected as shown below:

Column 5, lines 35-39, delete " 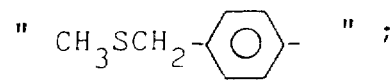 " ;

Column 5, lines 45-50, change the formula " 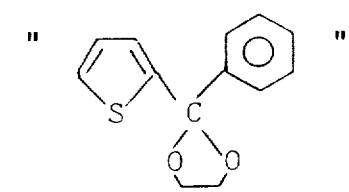 "

to -- 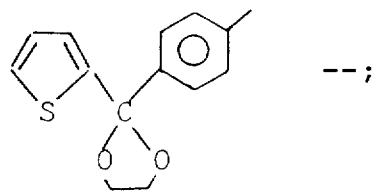 -- ;

Column 5, line 55, change the formula " 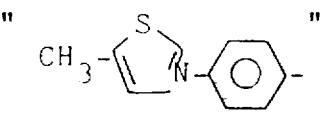 "

to -- 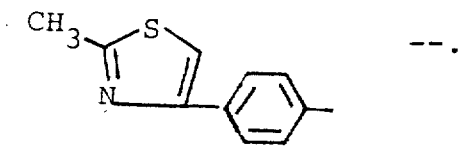 --.

UNITED STATES PATENT AND TRADEMARK OFFICE
CERTIFICATE OF CORRECTION

PATENT NO. : U.S.P. 4,433,160
DATED : February 21, 1984
INVENTOR(S) : TAKEHIRO AMANO ET AL.

It is certified that error appears in the above-identified patent and that said Letters Patent is hereby corrected as shown below:

Column 6, line 40, change formula " 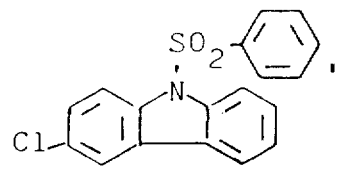 "

to -- 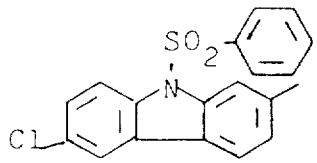 --.

Column 8, line 13, change "fulfate" to -- sulfate --.

Signed and Sealed this

Twenty-sixth Day of February 1985

[SEAL]

Attest:

DONALD J. QUIGG

Attesting Officer     Acting Commissioner of Patents and Trademarks